United States Patent [19]

Gennery

[11] Patent Number: 5,919,804
[45] Date of Patent: Jul. 6, 1999

[54] USE OF LEVOBUPIVACAINE IN FACIAL SURGERY

[75] Inventor: Brian Albert Gennery, Cambridge, United Kingdom

[73] Assignee: Darwin Discovery Limited, United Kingdom

[21] Appl. No.: 09/033,917

[22] Filed: Mar. 3, 1998

[30] Foreign Application Priority Data

Mar. 3, 1997 [GB] United Kingdom .................... 9704352

[51] Int. Cl.$^6$ .................................................. A61K 31/445
[52] U.S. Cl. ............................................................ 514/330
[58] Field of Search ............................................... 514/330

[56] References Cited

U.S. PATENT DOCUMENTS

4,695,576  9/1987  af Ekenstam et al. .................. 514/330

FOREIGN PATENT DOCUMENTS

9510276  4/1995  WIPO .
9510277  4/1995  WIPO .
9632109  10/1996  WIPO .

OTHER PUBLICATIONS

Butterworth, J. F. et al. (1993) "Bupivacaine InhibitsCyclic–3', 5' Adenosine Monophosphate Production" Anesthesiology 79:88–95.

Mazoit, J. X. et al. (1993) "Myocardial Uptake of Bupivacaine: II Pharmacokinetics and Pharmacodynamics of Bupivacaine Enantiomers in the Isolated Perfused Rabbit Heart" Anesth. Analg. 77(3):477–482.

Clarkson, C. W. et al. (1985) "Mechanism for Bupivacaine Depression of Cardiac Conduction: Fast Block of Sodium Channels during Action Potential with Slow Recovery from Block during Diastole" Anesthesiology 62:396–405.

Courtney, K.R. et al. (1988) "Bupivacaine is an effective potassium channel blocker in heart" Biochimica et Biophyscia Acta 939:163–166.

Denson, D. D. et al. (1992) "Enantiomer–Specific Effects on an Intravenously Administered Arrhythmogenic Dose of Bupivacaine on Neurons of the Nuleus Tractus Soluatroius and the Cardiovascular System in the Anesthetized Rat" Regional Anesthesia 17:311–316.

Vanhoutte, F. et al. (1991) "Stereoselective effects of the enantiomers of bupivacaine on the electrophysiological properties of the guinea–pig papillary muscle" Br. J. Pharmacol. 103:1275–1281.

Valenzuela, C. et al. (1994) "Stereoselective Bupivacaine Block of the Human Cardiac Delayed Rectifier Kv1.5 Channel" Biophys. J. 66:A205, abstract No. Tu–Pos383.

Aps, C. et al. (1978) "An Intradermal Study of the Local Anaesthetic and Vascular Effects of the Isomers of Bupivacaine" Br. J. clin. Pharmac. 6:63–68.

Burm, A.G.L. et al.(1994) "Pharmacokinetics of the enantiomers of bupivacaine following intravenous administration of the racemate" Br. J. Clin. Pharmac. 38:125–129.

Reynolds, F. (1995) "In defence of bupivacaine" International Journal of Obstetric Anesthesia 4:93–108.

Kuhnert, B.R. et al. (1981) "Bupivacaine disposition in mother, fetus, and neonate" Federation Proceedings, vol. 40, No. 31, p. 684.

Ariens, E. J. (1991) "Racemic therapeutics–ethical and regulatory aspects" Eur. J. Clin. Pharmacol., vol. 41, No.2, pp. 89–93.

Rutten, A. J. et al. (1991) "Cardiovascular Effects and Regional Clearances of I.V. Bupivacaine in Sheep: Enantiomeric Ananlysis" Br. J. Anasth., vol. 67(3):247–256.

Luduena, A. J. et al. (1972) "Optical Isomers of Mepivacaine and Bupivacaine" Arch. Int. Pharmacodyn. Ther., 200(2):359–369.

Rutten, A. J. et al. (1992) "Postoperative course of plasma protein binding of lignocaine, ropivacaine and bupivacaine in sheep" J. Pharm. Pharmacol., 44(4):355–358.

Lee–Son, S. et al. (1992) "Stereoselective Inhibition of Neuronal Sodium Channels by local Anaesthetics" Anesthesiology, 77(2):324–335.

Wang, G. K. et al. (1992) "Altered Stereoselectivity of Cocaine and bupivacaine Isomers in Normal and Barachotoxin–modified Na+ Channels" J. Gen. Physiol., 100(6):1003–1020.

Chemical Abstracts, 73(5), Aug. 3, 1970, Columbus, Ohio, U.S.; abstract No. 25314a.

Clark, B. J. et al. (1991) "Reversed–phase and chiral high–performance liquid chromatographic assay of bupivacaine and its enantiomers in clinical samples after continuous extrapleural infusion" J. Chromatog., 553:383–390.

Ariens, E. J. (1990) "Racemische therapeutica probleemmiddelen" Pharmaceutisch Weekblad, 125(2):552–554.

Ariens, E. J. (1990) "Stereoselectivity in pharmacodynamics and pharmacokinetics" Schweiz. med. Wochenschr., 120(5):131–134.

Rowland, M. et al.(eds.) In: Clinical Pharmacokinetics Concepts and Applications, Chapter 7, pp. 83–88, (1995) Williams & Wilkins publishers.

Mather, L. E. (1991) "Disposition of Mepivacaine and Bupivacaine Enantiomers In Sheep" British Journal of Anaesthesia 67:239–246.

Du Pen, S. L. et al. (1992) "Chronic epidural bupivacaine–opioid infusion in intractable cancer pain" Pain 49:293–300.

Honerjäger, P. (1986) "The contribution of Na channel block to the negative inotropic effect of antiarrhythmic drugs" Basic Res. Cardiol. 81 (Suppl 1):33–37.

Fozzard, H.A. et al. (1985) "Voltage Dependence of Intracellular Sodium and Control of Contraction" In Zipes DP, Jalife E (eds) Grune & Stratton, Orlando, pp. 51–57.

(List continued on next page.)

*Primary Examiner*—Phyllis G. Spivack
*Attorney, Agent, or Firm*—Saliwanchik, Lloyd & Saliwanchik

[57] ABSTRACT

Levobupivacaine is used for providing anesthesia or analgesia in a human patient in and after facial surgery, especially in dentistry or ophthalmics.

5 Claims, No Drawings

OTHER PUBLICATIONS

Schlepper, M. (1989) "Cardiodepressive effects of antiarrhythmic drugs" European Heart Journal 10(Suppl. E.):73–80.

Reiz, S. et al. (1986) "Cardiotoxicity Of Local Anaesthetic Agents" Er. J. Anaesth. 58:736–746.

De Jong, R. H. et al. (1981) "Treating Bupivacaine Arrhythmias: Preliminary Report" Reg Anesth 6:99–103.

Strichartz, G. R. (1988) :Neural physiology and local anesthetic action In: Neural Blockade In Clinical Anesthesia And Management Of Pain, Cousins MJ, Bridenbaugh PO (eds), J B Lippincott Company, Philadelphia, pp. 25–45.

Gristwood, R, et al. (1994) "Reduced cadiotoxicity of levobupivavcaine compared with racemic bupivacaine (Marcaine): new clinical evidence" Exp. Opin. Invest. Drugs 3(11):1209–1212.

Testa, B. et al. (1990) "Racemates Versus Enantiomers in Drug Development: Dogmatism or Pragmatism?" Chirality 2:129–133.

Rutten, A. J. et al. (1993) "Tissue distribution of bupivacaine enantiomers in sheep" Chirality 5(7):485–491.

Aberg, G. (1972) "Toxicological and local anaesthetic effects of optically active isomers of two anaestheitic compounds" Acta Pharmacologica Et Toxicologica 31:273–286.

USE OF LEVOBUPIVACAINE IN FACIAL SURGERY

FIELD OF THE INVENTION

This invention relates to a new therapeutic use for levobupivacaine or (S)-1-butyl-N-(2,6-dimethylphenyl)-2-piperidinecarboxamide.

BACKGROUND OF THE INVENTION

Racemic bupivacaine is an effective long-acting local anaesthetic, and may be given as an epidural. However, racemic bupivacaine is cardiotoxic, having depressant electrophysiological and mechanical effects on the heart. It should therefore be used with caution in cardiac-compromised patients, and the use of high doses and high concentrations is contraindicated.

In particular, bupivacaine has produced death in a number of patients, including women in childbirth and when used in the Bier's block technique. Although the incidence of death has been relatively small, the concern has been sufficient to stop the use of 0.75% bupivacaine for obstetrics and the proscribing of bupivacaine for use in Bier's blocks.

In addition, due to its mode of action, directly on the nervous system, at higher doses, bupivacaine is known to have undesirable central nervous system (CNS) side-effects which, *prima facie,* are connected to its anaesthetic activity. Indeed, the occurrence of CNS side-effects is one of the major factors limiting the use of this drug in normal clinical practice employing techniques such as local infiltration, nerve block, field block, epidural and spinal blocks.

It has been suggested that levobupivacaine is less cardiotoxic than dextrobupivacaine and racemic bupivacaine. See, for example, Vanhoutte et al., Br. J. Pharmacol. 103:1275–1281 (1991), and Denson et al, Regional Anaesthesia, 17:311–316 (1992). However, these reports are based on work in vitro, and cannot necessarily be extrapolated to any mammals, and certainly not to humans.

The surprising and effective utility of levobupivacaine in man, in vivo, is evidenced for the first time in WO-A-9510276, WO-A-9510277 and Gristwood et al, Exp. Opin. Invest. Drugs 3(11):1209–12 (1994).

An effective, safe, long-acting anaesthetic would be particularly valuable for use in facial surgery. However, the administration of such a compound for local anesthesia, and post-operative analgesia, presents particular problems; small volume should be administered, owing to the mass of nerves and/or blood vessels, e.g. around the eyes and in the gums. This is associated with low efficacy. High drug concentrations are therefore necessary.

Lignocaine is widely used, especially in dentistry. However, it is associated with neurotoxicity. In order to give adequate depth of block and duration of action, it is usually administered together with epinephrine. This gives rise to further undesirable effects such as palpitations and syncope. A safer drug would be desirable.

SUMMARY OF THE INVENTION

While it has previously been shown that the use of levobupivacaine may have advantages over bupivacaine in certain areas, there has been no evidence to suggest that it would be of value, in facial surgery in general, and especially in ophthalmics and dentistry. This invention is based on the surprising discovery that levobupivacaine is an effective and especially safe anaesthetic, for this purpose. In particular, it is less neurotoxic than bupivacaine and it is safer in this regard than lignocaine (when given alone or in combination with dextrose or epinephrine). It may have a vasoconstrictive effect. This is useful where the site of administration has a high mass of nerves and/or blood vessels, since no or less epinephrine is required. There is reduced potential for side-effects, in clinical dosage ranges.

DESCRIPTION OF THE INVENTION

In the method of the present invention, levobupivacaine may be provided in solution, for infusion or injection into the epidural or spinal space, or for administration by any of the conventional means for obtaining a nerve or field block. In addition to the anaesthetic blocks conventionally provided by the racemate, levobupivacaine may also be useful in providing blocks in areas of the body where the risk of systemic exposure to the drug, and therefore CNS side-effects, is particularly high. Examples include open wounds and vascular areas, for instance using intercostal blocks for the latter. Especially for ophthalmic use, it may be applied topically.

Administration of levobupivacaine may be continuous or bolus administration. This may be done using conventional apparatus, e.g., including means for the patient to induce infusion as desired. The daily dose administered to the patient may be in the relatively low range known for the administration of racemic bupivacaine, but, because of the decreased CNS side-effects of levobupivacaine, may be higher than the conventional dose for the racemic drug. The total dose of levobupivacaine may be around, or in excess of, 2 mg per kg of patient body weight.

The concentration of levobupivacaine to be given can be that conventionally used for the racemic drug, e.g. from 0.25% w/v. However, especially for ophthalmics, the concentration may be higher than this, for instance, at least 0.75% w/v, and can be up to 1.5% w/v. Preferably, however, the concentration of levobupivacaine is in the range 0.5% to 1% w/v. The solution is preferably aqueous.

The solution may typically be put up in unit doses of from 1 to 15 ml, and preferably of around 10 ml. However, the unit doses may be higher, for instance up to 40 ml or higher. The unit doses may be in the form of ampoules, which may be made of any suitable material, e.g. glass or an appropriately impervious plastic material. Unit dosages comprising at least 25 mg, but preferably less than 200 mg, of levobupivacaine can be administered, and more preferably the unit dosage is in the range 25 to 100 mg.

The administration of levobupivacaine over a range of concentrations, including those currently used for the racemic drug and the higher concentrations described above, can be carried out for significantly longer periods than at present, again as a result of the reduced CNS side-effects experienced with levobupivacaine. For instance, levobupivacaine can be administered to a patient safely for at least 24 hours, often up to 72 hours, or longer. It can, of course, be administered for similar periods already used for the racemic drug, e.g. between 3 and 10 hours. Levobupivacaine may be particularly valuable for the maintenance of post-operative analgesia.

The method of the present invention is particularly useful in surgical procedures carried out on patients who merely require surgery, and are otherwise healthy. The patient may also be cardiac or CNS-compromised, or predisposed to cardiac or CNS-related conditions, i.e. having a low CNS threshold.

Levobupivacaine is suitable for use, according to the invention, in connection with dental surgery, e.g. for the removal of wisdom teeth. It may also be used during corrective eye-surgery, e.g. the removal of cataracts in perior retrobulbar blocks.

Levobupivacaine and racemate may be equipotent, but levobupivacaine can have preferable characteristics such as minimal effect on the neurovascular system, and a good haemodynamic profile.

For the purposes of this specification, the levobupivacaine is substantially free of dextrobupivacaine, i.e. in at least 90%, and most preferably at least 99%, enantiomeric excess. Throughout this specification, reference to bupivacaine and its enantiomers includes pharmaceutically-acceptable salts thereof.

A study has been conducted, to compare the efficacy of 0.75% levobupivacaine with 2% lignocaine (with adrenaline) and placebo (0.9% NaCl) as post-operative pain relief in patients who underwent unilateral or bilateral impacted 3rd molar extractions, and to compare the safety of the study medication. This was a single-centre, randomised, double blind study. 30 patients were randomised per group, and the randomisation was stratified for unilateral and bilateral extractions. Visual analogue scale pain scores were conducted. The time of all rescue medication was recorded and the time of offset of the block was recorded.

For each impacted mandibular tooth, 2 ml was administered as an inferior alveolar nerve block and 1 ml was administered as buccal infiltration. For each maxillary tooth, 1 ml was administered as buccal infiltration and 0.5 ml as palatal infiltration.

Levobupivacaine, lignocaine and placebo had similar safety profiles in patients undergoing unilateral or bilateral impacted 3rd molar extractions. However, setting the time to rescue medication to the time from surgery completion to withdrawal or to 48 h for patients who did not take rescue medication, the mean time to first requirement for rescue analgesia was almost 3 times higher for patients in the levobupivacaine group compared with those in the other 2 treatment groups. The median was lowest for the placebo group (45 min) and then the lignocaine group (55 min) but was much higher for the levobupivacaine group (87.5 min). The standard deviation was about 5 times larger for the levobupivacaine group than the others, and this is because the maximum time to rescue medication in this group was 48 h whereas the maximum value was under 8 h for the other treatment groups.

In further studies, 0.75% levobupivacaine was compared with 0.75% bupivacaine, in patients undergoing ophthalmic anterior segment surgery, with peribulbar block, to determine their relative efficacy. No significant differences were found, in the time of onset to block. The relative value of levobupivacaine is seen as the result of another study, comparing the effects of 0.5% levobupivacaine and 0.5% racemic bupivacaine on QT dispersion and single averaged ECG in healthy male volunteers.

This last study involved intravenous infusion of 10 mg/min up to a maximum of 150 mg drug, singly on 2 occasions. Evaluation involved ECG monitoring. In particular, autonomic NS disorders (flushing), central disorders (headache, chest pain), central/peripheral NS disorders (dizziness, hypoaesthesia, paraesthesia), hearing disorders (tinnitus), other disorders (taste perversion), were observed.

Significantly reduced peripheral/control nervous system disorders and hearing disorders (tinnitus) were seen with levobupivacaine. These symptoms are commonly seen in the clinical setting, with currently used agents (for which these are restrictions in head and neck surgery).

The overall frequency of events is tabulated below.

|  | Bupivacaine 0.5% (n = 22) | | Bupivacaine 0.5% (n = 11) | | Levobupivacaine 0.5% (n = 11) | |
| --- | --- | --- | --- | --- | --- | --- |
|  | n | % | n | % | n | % |
| Patients with no events | — | — | 1 | 9 | 4 | 36 |
| Patients with 1 or more events | 22 | 100 | 10 | 91 | 7 | 64 |

For those subjects who received more than 75 mg, the QTc results are:

| Bupivacaine more than 75 mg | 0.024 |
| --- | --- |
| Levobupivacaine more than 75 mg | 0.003 |
| P value | 0.022 |

The importance of these results lies also in the fact that, for facial surgery, large single doses of drug may be given, e.g. 75 mg or more. Clinically, 10 ml of 0.75% or 1% levobupivacaine would be desirable.

I claim:

1. A method of providing anesthesia or analgesia in a human patient in or after facial surgery, which comprises the administration of levobupivacaine, wherein said levobupivacaine is present in an enantiomeric excess of at least about 90% with respect to dexbupivacaine.

2. The method, according to claim 1, wherein said surgery is dental surgery.

3. The method, according to claim 1, wherein said surgery is ophthalmic surgery.

4. The method, according to claim 1, which comprises administering a single dose of levobupivacaine.

5. The method, according to claim 4, wherein said dose comprises at least 75 mg of levobupivacaine.

* * * * *